United States Patent [19]

Lehto

[11] Patent Number: 5,369,278
[45] Date of Patent: Nov. 29, 1994

[54] CALIBRATION METHOD FOR GAS CONCENTRATION MEASUREMENTS

[75] Inventor: Ari Lehto, Helsinki, Finland

[73] Assignee: Vaisala Oy, Helsinki, Finland

[21] Appl. No.: 1,636

[22] Filed: Jan. 7, 1993

[30] Foreign Application Priority Data

Jan. 30, 1992 [FI] Finland ................................ 920410
Oct. 22, 1992 [FI] Finland ................................ 924788

[51] Int. Cl.$^5$ ..................... G01D 18/00; G01N 21/61
[52] U.S. Cl. ..................................... 250/343; 356/311
[58] Field of Search ................ 250/343; 356/311, 437

[56] References Cited

U.S. PATENT DOCUMENTS

| | | | |
|---|---|---|---|
| 3,836,255 | 9/1974 | Schuman | 356/311 |
| 4,500,207 | 2/1985 | Maiden | 356/409 |
| 4,709,150 | 11/1987 | Burough et al. | 250/338.1 |
| 4,711,571 | 12/1987 | Schuman | 356/311 |

OTHER PUBLICATIONS

R. Whyman, K. A. Hunt, R. W. Page and S. Rigby, "A high-pressure spectroscopic cell for FTIR measurements." *J. Phys. E: Sci. Instrum.*, vol. 17, No. 7, (Jul. 1984).

*Primary Examiner*—Constantine Hannaher

[57] ABSTRACT

A calibration method for gas concentration measurement with an NDIR technique based on optical absorption. Radiation is imposed onto the gas mixture under measurement contained in a measurement channel (3) isolated at least partially from its environment, the intensity of radiation transmitted through the gas is measured, the gas concentration is computed from the measured intensity, in order to calibrate the measurement apparatus the gas state variables are deviated in a controlled manner, whereby the level of transmitted radiation intensity is changed, and the intensity of the transmitted radiation is measured in at least two known points of the gas state variables, thus obtaining data for calibration of the measurement apparatus employed. The gas state variables are deviated by heating the gas under measurement in such a short time during which the ambient concentration of the gas undergoes no change, whereby the gas density is decreased with the increasing temperature, while the partial pressure of the gas under measurement stays essentially constant.

5 Claims, 2 Drawing Sheets

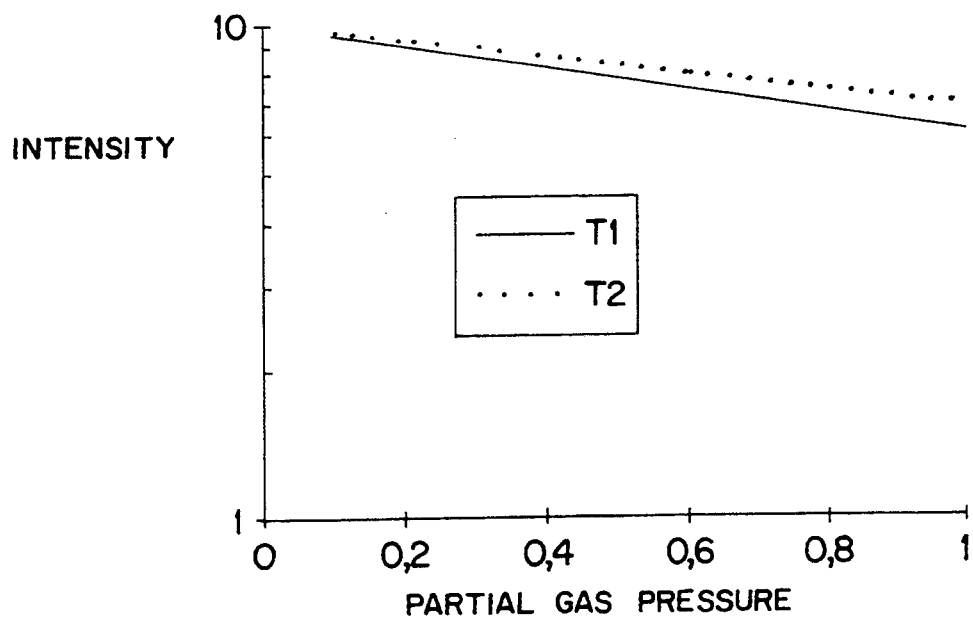
FIG. 1
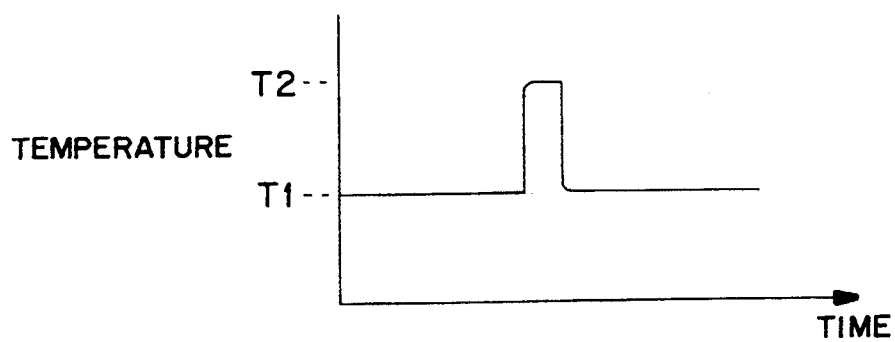
FIG. 2.a
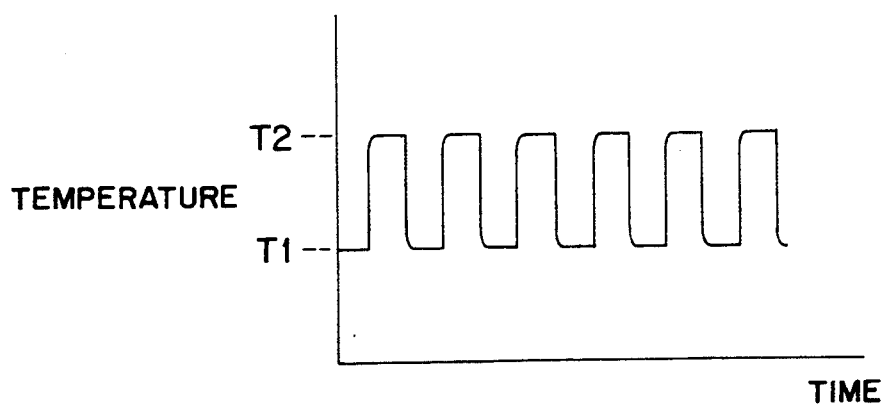
FIG. 2.b

CALIBRATION METHOD FOR GAS CONCENTRATION MEASUREMENTS

The invention relates to a self-calibrating gas concentration measurement method according to claim 1 based on optical absorption. The invention is particularly intended for use as a self-calibrating method of nondispersive IR measurements (NDIR).

BACKGROUND OF THE INVENTION

In NDIR measurements the wavelength range is selected to cover the maximum absorption band in the gas to be measured. Absorption causes loss in transmitted intensity of radiation, thus offering a method for determination of gas concentration. Typically, the radiation source is an incandescent lamp and the desired wavelength range is selected with the help of a filter. The method is handicapped by measurement errors caused by intensity variations in the lamp output and contamination of the optical channel. Furthermore, changes in detector sensitivity may reduce measurement accuracy.

Due to the instability of an NDIR measurement system, the equipment must be calibrated frequently with the help of calibration gases. An alternative method is the use of a reference channel which permits separate monitoring of the input radiation intensity to the actual measurement channel containing the gas under measurement.

A prior-art embodiment employs in the reference channel a filter whose bandpass wavelength is selected so that the measurement is performed at wavelength corresponding to an absorption minimum in spectrum of the radiation transmitted through the gas. Thus, the value of transmitted intensity measured at the reference wavelength can be compared with the value measured as an absorption band of the gas. The method necessitates the use of two separate filters, and the shifting of the filters makes the system mechanically complicated.

The U.S. Pat. No. 4,709,150 discloses an embodiment in which the prevention of the optical channel contamination is attempted through making the measurement channel from a porous material that is easily penetrable for the gas to be measured, while being capable of preventing major contamination components of ambient air from entering the measurement channel. The porous material can be made from an appropriate plastic material or porous stainless steel. The method fails, however, to remove measurement error caused by a decline of lamp output intensity.

The U.S. Pat. No. 4,500,207 describes a measurement apparatus and method in which the internal gas pressure of the measurement channel is modulated at constant temperature with the help of a movable membrane placed on the wall of the measurement channel. Pressure modulation in an NDIR measurement varies the density of the gas under measurement, whereby additional information can be gathered from the gas to be measured that can be used for eliminating instability caused by lamp aging and contamination. Although the movable membrane can be constructed in the same manner as a loudspeaker, the system becomes mechanically complicated. Another disadvantage is that, to implement the gas pressure modulation, the measurement channel must be isolated from the ambient surroundings using a channel of slow gas diffusion. This causes the system to have a relatively long response time to changes in the ambient gas concentration.

SUMMARY OF THE INVENTION

It is an object of the present invention to overcome the disadvantages of the above-described techniques and to achieve a novel method of gas concentration measurement.

The invention is based on heating the measurement channel and performing the optical absorption measurements using at least two different temperatures. The measurement channel temperature can be measured independently. The invention utilizes the fact that heating of the gas in the measurement channel reduces the density of the gas and changes the absorption coefficient of the gas under measurement. The measurement channel is heated so rapidly that the concentration of the gas under measurement has insufficient time to undergo a concentration change during the absorption measurement performed at the different temperatures. Intensity measurement of transmitted radiation using at least two different internal channel temperatures and yielding two different values of absorption coefficient gives sufficient additional information for elimination of measurement equipment instability factors.

More specifically, the method in accordance with the invention is characterized by what is stated in the characterizing part of claim 1.

The invention offers significant benefits.

The invention facilitates calibration of measurement equipment in measurement conditions, disposing with the need for using separate calibration gases. The invention draws upon the fact the heating of and temperature measurement in the measurement channel can be performed easily and at low cost. The measurement equipment based on the present measurement method can be made simple and rugged, because movable components need not be employed. The measurement channel and its resistive heating element can be constructed so that temperature change and calibration of the gas under measurement can be performed rapidly in relation to the gas concentration change rate. Calibration performed sufficiently frequently removes measurement inaccuracy caused by the inherent instability of the NDIR measurement equipment and decisively extends the maintenance interval of the equipment.

The invention also concerns a measurement method in which the measurement channel internal temperature is continuously modulated between at least two different temperatures. Then, the measurement method corresponds to a calibration method in which calibration is performed after each measurement. The apparatus based on the invention can be designed so that each heating cycle takes about one minute. In many applications of the NDIR measurement method, a measurement rate of gas concentration of approximately once a minute is considered sufficient.

BRIEF DESCRIPTION OF THE DRAWINGS

In the following the invention is examined in greater detail with the help of an exemplifying embodiment illustrated in the annexed drawing, in which FIG. 1 shows in graphic form the intensity of radiation reaching the detector vs. the partial pressure of the absorbing gas component for two different internal temperatures of the measurement channel.

FIG. 2a shows in graphic form the internal temperature of the measurement channel vs. time for the calibration method according to the invention, and correspondingly, FIG. 2b for the measurement method according to the invention.

DETAILED DESCRIPTION OF THE INVENTION

Figure 3:
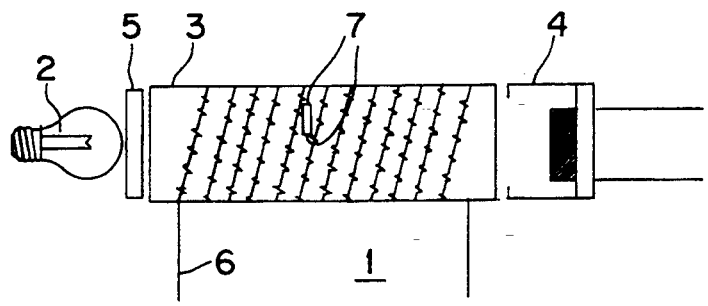
FIG. 3 shows a measurement head structure based on the calibration method according to the invention.

When a wavelength band on which the gas under measurement exhibits absorption on transmitted radiation is considered, the input intensity of radiation $I_0$ to the measurement channel and the output intensity of radiation I exiting the channel follow the Lambert-Beer absorption law $$I = I_0^{-\alpha(T)pl} \qquad (1)$$

where $\alpha(T)$ is the absorption coefficient of the gas under measurement, dependent on the temperature T; p is the partial pressure of the gas under measurement; and l is the length of the measurement channel. FIG. 1 illustrates at two different temperatures the intensity of radiation exiting from the measurement channel as a function of partial gas pressure. Absorption in the gas at elevated temperature is seen decreased.

When the measurement temperature is $T_1$ and the intensity measured by the detector is $I_1$, the partial gas pressure can be determined from the equation $$p = \frac{1}{\alpha(T_1)l} \times (\log(I_0) - \log(I_1)) \qquad (2)$$

The output signal of the NDIR measurement apparatus is typically conditioned to indicate gas concentration, which is linearly proportional to the partial gas pressure measured at a certain total pressure and temperature of the measured gas mixture. Linearization on the basis of the equation 2 can be made with the help of analog electronics, while digital processing using a microprocessor is the easiest way to linearization. The chief source of instability in an NDIR measurement apparatus results from the variations of input radiation intensity ($I_0$) to the measurement channel, which typically causes an offset-type measurement error.

An initial assumption can be made that, during the heating of the measurement channel in the calibration sequence according to FIG. 2a, the concentration of the gas component to be measured stays approximately constant in the measurement site. Then, also the partial pressure of the gas to be measured stays constant if the gas mixture total pressure is maintained constant during the heating cycle. The calibration measurement is carried out so rapidly that also the lamp output intensity can be assumed to stay approximately constant. Having the measurement channel heated to temperature $T_2$ and the detector sensing an intensity level $I_2$ for the detected radiation, the equation 2 is rewritten for these values $$p = \frac{1}{\alpha(T_2)l} \times (\log(I_0) - \log(I_2)) \qquad (3)$$

The absorption coefficient $\alpha(T)$ changes with the heating of the measurement channel, causing the detector output signal for the measured radiation intensity to be different at the different temperatures. When the temperatures $T_1$ and $T_2$ can be assumed to be known, the term $\log(I_0)$ can be solved from the equations 2 and 3

$$\log(I_0) = \frac{\log(I_1) - \frac{\alpha(T_1)}{\alpha(T_2)} \times \log(I_2)}{1 - \frac{\alpha(T_1)}{\alpha(T_2)}} \qquad (4)$$

To make use of equation 4, the change rate of the absorption coefficient as a function of temperature must be known. The value of the term $\log(I_0)$ can then be computed with the help of a microprocessor and then, using the computed value, the value of partial gas pressure obtained from equation 2 can be corrected.

In an alternative measurement method according to the invention illustrated in FIG. 2b, the measurement channel temperature is continuously modulated and the gas concentration is computed at a low temperature $T_1$ and a high temperature $T_2$ from the intensities $I_1$ and $I_2$ of radiation measured at these temperatures. Equations 2 and 4 are combined to solve the partial gas pressure $$p = \frac{1}{\alpha(T_1)l} \times \frac{1}{\frac{\alpha(T_2)}{\alpha(T_1)}} \times \log\left(\frac{I_1}{I_2}\right) \qquad (5)$$

The accuracy of the calibration and measurement method is improved essentially if the temperatures $T_1$ and $T_2$ in the measurement channel are measured by a separate temperature sensor, and the value of the absorption coefficient is computed at the measured temperatures.

Applications with relaxed accuracy requirements can be implemented using the method according to the invention without separate temperature measurement. In this embodiment, the measurement channel is heated during each heating cycle with a constant input power, whereby the measurement channel heats in a certain time to an approximately constant level of elevated temperature, at which the intensity measurement of radiation is performed. Here, however, changes in ambient temperature cause inaccuracy in such a calibration and measurement method.

To implement the calibration and measurement method according to the invention, the effect of temperature on the absorption coefficient must be known accurately. Fortunately, the absorption imposed on the radiation travelling along the measurement channel is linearly proportional to the number of absorbing gas molecules contained in the measurement channel volume, so the effect of the gas density on the absorption coefficient simply results thereof.

In a constant volume and at a constant pressure, the number of gas molecules decreases with increasing temperature according to the ideal gas law $$pV = nRT \qquad (6)$$

where p is pressure, V is volume, n is the number of gas molecules in moles, R is the gas constant and T is the absolute temperature. The ideal gas law applies to both the total pressure of the gas mixture and the partial pressure of the gas component to be measured. According to the equation 6, the product of the density $\rho$ and the temperature of the gas under measurement in the measurement channel stays constant with varying temperature at a constant pressure:

$$\rho_1 T_1 = \rho_2 T_2 \qquad (7)$$

In the above equation, $\rho_1$ is the density of the gas component to be measured at temperature $T_1$ and $\rho_2$ is the density at temperature $T_2$.

In addition to affecting the number of gas molecules occupying a constant volume, temperature also has an effect on the molar absorption coefficient. This is because the absorption spectrum of a molecule in the infrared range is composed of spectral lines of different wavelengths attributable to different rotational-vibrational transitions. Each of these spectral lines is affected differently by temperature. If multiple spectral lines fall within the wavelength band employed for measurement, the temperature dependence of each spectral line must be determined separately. Theoretical methods are available for the determination of the total effect of the temperature dependences of the different spectral lines on the molar absorption coefficient over the employed wavelength range. Experimental methods offer, however, the easiest solution to the determination of the temperature dependence.

An exemplifying situation is considered by taking into account the effect of gas density variations on the absorption coefficient. The gas under measurement is assumed to be carbon dioxide with a concentration of 1000 ppm in the measurement channel at 300K. The emitting source is a black-body radiator. A filter tuned to pass the desired absorption band of $CO_2$ only is placed between the radiation source and the detector. Equation 1 can be employed for computing the intensity of radiation reaching the detector when the following parameter values are assumed:

$T_1 = 300K$
$T_2 = 350K$
$I_0 = 100 \mu W$
$l = 5$ cm $$\alpha(T_1) = 2.0 \ast 10^{-5} \, cm^{-1} ppm^{-1} \qquad (T=300K)$$

The ratio of absorption coefficients for the examined case is solved from equation 7:

$$\frac{\alpha(T_1)}{\alpha(T_2)} = \frac{T_2}{T_1} \qquad (8)$$

At the two different temperatures the values of radiation intensity measured by the detector are:

| Temperature | Radiation intensity |
| --- | --- |
| 300 K. | 90.5 $\mu W$ |
| 350 K. | 91.8 $\mu W$ |

The sensitivity of a photoconductive or pyroelectric detector is sufficient for detecting the above given change in radiation intensity, and the calibration according to the invention can be carried out with sufficient accuracy.

The accuracy of the calibration method according to the invention is improved with an increase in the temperature difference between $T_1$ and $T_2$, which should be at least 50° C.

The output voltage from the detector increases approximately linearly with the intensity of measured radiation. This property gives the present calibration and measurement method a benefit in that the method is capable of removing measurement inaccuracy caused by detector sensitivity changes. For instance, the output signal of a photoconductive or pyroelectric detector follows accurately the formula $$V = GI \qquad (9)$$

where V is the output voltage from the detector and G is the detector sensitivity. Elimination of detector sensitivity change is related to the fact that the equation 5 incorporates only the ratio of the radiation intensities $I_1$ and $I_2$ measured at the different temperatures, and the absolute value of neither of these intensities need be known separately.

FIG. 3 shows a possible way of implementing a measurement section suited to implement the calibration and measurement method according to the invention. An incandescent lamp (black body radiator) is employed as a radiation source 2, and the desired wavelength band is selected with the help of a filter 5. The radiation source can also be a spectral emitter containing the gas under measurement or a semiconductor infrared LED emitter. The radiation intensity passing through the measurement channel 3 is measured with the help of a detector 4. The detector can be, e.g., a commercially available photoconductive or pyroelectric detector. The wall of the measurement channel can be made from a porous material easily permeable by diffusion of the gas under measurement. This arrangement makes the heating of the gas mixture in the measurement channel easy, because a diffusing wall reduces heat convection to the environment from the measurement channel. The measurement channel is preferably made from porous plastic or stainless steel. Advantageously, the calibration method should have a thermal mass as low as possible in the measurement channel so making the heating of the measurement channel maximally rapid. FIG. 3 shows the heating arrangement implemented by means of a resistive conductor 6 wound about the measurement channel. The temperature measurement can be implemented using a resistive platinum element 7 or any other commercial temperature sensor. A single resistive element can also be employed for both heating the measurement channel and measuring its internal temperature. The required length of the measurement channel depends on the absorption coefficient and desired concentration measurement range of the gas component under measurement. For instance, the measurement channel length can be as short as 5 cm for $CO_2$ concentration measurements of the ambient air.

To speed the heating cycle required in the present calibration method, also the lower temperature $T_1$ can be kept above the ambient temperature. Then, the cooling time from the upper temperature $T_2$ to the lower temperature $T_1$ is also shortened.

The calibration method based on two different temperatures can be expanded into a calibration sequence based on multiple temperatures. This approach can be utilized to improve the linearity of the NDIR measurement apparatus output signal.

Figure 4:
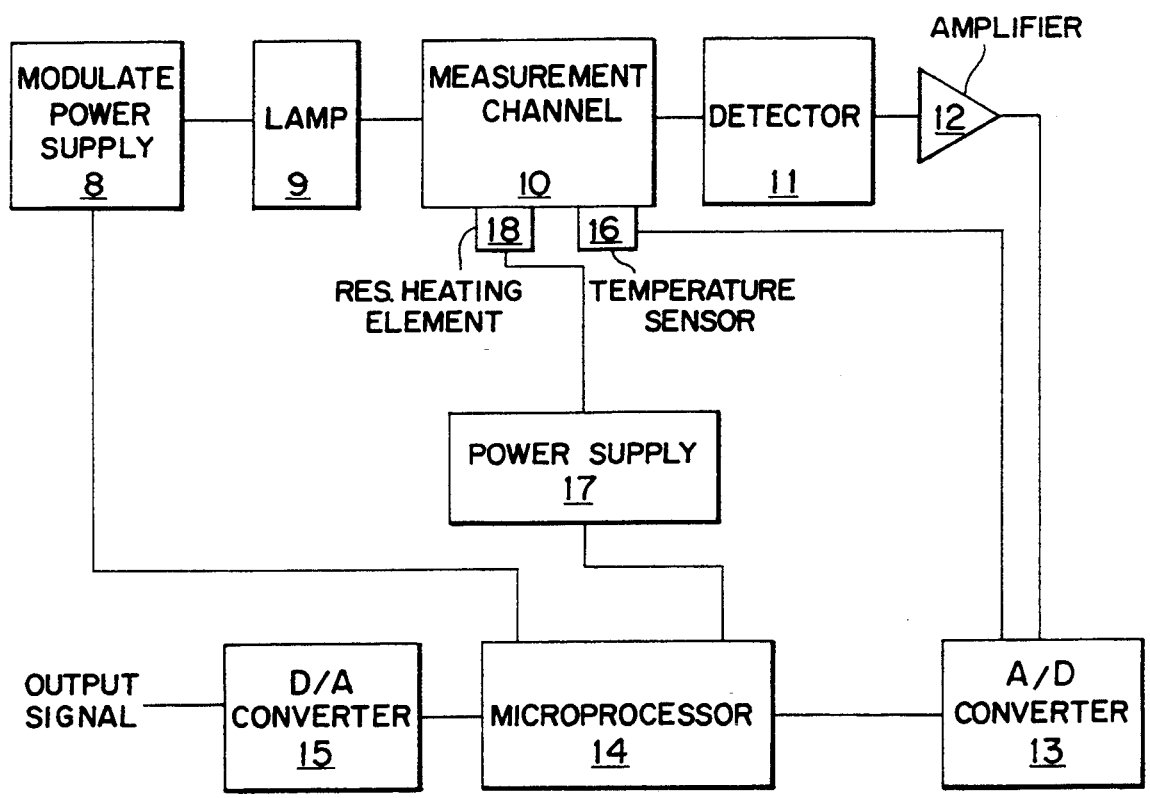
FIG. 4 shows a gas concentration measurement apparatus based on the measurement head illustrated in FIG. 3.

FIG. 4 shows a block diagram of an apparatus in which the optical sensor can be of the same type as that in FIG. 3 and in which the output signal is proportional to the concentration of the gas component under measurement. The microprocessor-based apparatus illustrated in FIG. 4 facilitates concentration measurements in accordance with the calibration or measurement method according to the invention.

The optical measurement section comprises an incandescent lamp 9, a measurement channel 10 and a detector 11. The internal temperature of the measurement channel is measured with the help of a temperature sensor 16, and the channel heating is implemented with a resistive heating element 18 fed by a power supply 17. The radiation intensity emitted by the incandescent lamp is modulated at a suitable rate with the help of a modulated power supply 8. The detector 11 measures the modulated intensity of the transmitted radiation and the output signal of the detector is amplified by an amplifier 12. The amplifier output voltage signal is converted into digital form by an A/D converter 13 and taken to a microprocessor 14. The output voltage of the temperature sensor 16 is also converted into digital form by the A/D converter 13 prior to taking it to the microprocessor 14. The microprocessor manages on time-shared basis the basic functions necessary in the calibration and measurement method according to the invention: heating of measurement channel, measurement of internal temperature in the channel and measurement of transmitted radiation intensity as well as the processing of measurement data. On the basis of the measurement data and using the abovedescribed algorithms, the microprocessor computes the concentration of the gas component under measurement. The measurement result is converted into an analog output signal of the measurement apparatus with the help of a D/A converter 15.

I claim:

1. A calibration method for gas component concentration measurement with a measurement apparatus corresponding to an NDIR technique based on optical absorption, comprising the steps of:

directing radiation on a gas under measurement including the gas component contained in a measurement channel in the measurement apparatus;

measuring the intensity of radiation transmitted through the gas under measurement; and deviating the temperature of the gas through a heating cycle; characterized in that the measurement channel permits gas expansion during the heating cycle to maintain a constant pressure during measurement, the measurement of the intensity of radiation transmitted through the gas is performed at least at two different temperatures, the measurement results being utilized for calibration of the measurement apparatus and then for computing the concentration of the gas under measurement, and the deviation of the gas temperature occurs during such a short interval of time that the concentration of the gas entering the system does not change, whereby the density of the gas under measurement decreases with increasing temperature while the partial pressure of the gas component under measurement remains essentially constant.

2. A method as defined in claim 1, characterized in that temperature of the gas under measurement is separately measured using a temperature sensor.

3. A method as defined in claim 1, characterized in that the measurement is performed in a measurement channel comprised of a diffusive wall channel heated with a resistive heating element, said channel wall being made of a material capable of permitting easy penetration of the gas under measurement but limiting thermal convection between the gas mixture contained in the channel and the ambient surroundings.

4. The method as defined in claim 1, characterized in that the temperature of the gas under measurement is deviated at a continuous rate and the output signal of the measurement apparatus is formed on the basis of the transmitted radiation intensities measured at the at least two different temperatures of the gas under measurement and of the at least two different temperatures of the gas under measurement.

5. The method as defined in claim 1, characterized in that the internal temperature of the measurement channel is continuously maintained above the ambient temperature of the apparatus.

* * * * *